United States Patent
Agnew

(12)
(10) Patent No.: US 8,257,314 B2
(45) Date of Patent: Sep. 4, 2012

(54) SPIRAL SHAFT CATHETER

(75) Inventor: Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 846 days.

(21) Appl. No.: 11/595,829

(22) Filed: Nov. 10, 2006

(65) Prior Publication Data

US 2007/0112306 A1  May 17, 2007

Related U.S. Application Data

(60) Provisional application No. 60/737,181, filed on Nov. 16, 2005.

(51) Int. Cl.
*A61M 5/178* (2006.01)
*A61M 31/00* (2006.01)
*A61M 37/00* (2006.01)
*A61F 2/02* (2006.01)

(52) U.S. Cl. ............... 604/164.13; 604/93.01; 604/509; 623/1.11

(58) Field of Classification Search ........... 604/164.13, 604/93.01, 509; 623/1.11
See application file for complete search history.

(56) References Cited

U.S. PATENT DOCUMENTS

| | | | |
|---|---|---|---|
| 5,554,114 A | 9/1996 | Wallace et al. | |
| 6,264,682 B1 * | 7/2001 | Wilson et al. | 623/1.11 |
| 6,475,187 B1 * | 11/2002 | Gerberding | 604/102.02 |
| 7,018,358 B2 * | 3/2006 | Joergensen et al. | 604/96.01 |
| 2002/0038103 A1 | 3/2002 | Estrada et al. | |
| 2003/0191451 A1 * | 10/2003 | Gilmartin | 604/527 |
| 2007/0060942 A2 * | 3/2007 | Zadno-Azizi | 606/194 |
| 2007/0088257 A1 * | 4/2007 | Fisher et al. | 604/103.04 |
| 2008/0221611 A1 * | 9/2008 | Kletschka | 606/200 |

FOREIGN PATENT DOCUMENTS

| | | |
|---|---|---|
| EP | 0 410 602 A1 | 7/1990 |
| WO | WO 03/002018 A2 | 1/2003 |
| WO | WO 03/080167 A2 | 10/2003 |

\* cited by examiner

*Primary Examiner* — Nicholas Lucchesi
*Assistant Examiner* — Ian Holloway
(74) *Attorney, Agent, or Firm* — Brinks Hofer Gilson & Lione

(57) ABSTRACT

A spiral catheter device and mechanism for placement thereof. The spiral catheter device comprises a catheter body including at least one helically coiled portion, with the interior region of the helix forming a tracking region for passage of a wire guide.

24 Claims, 10 Drawing Sheets

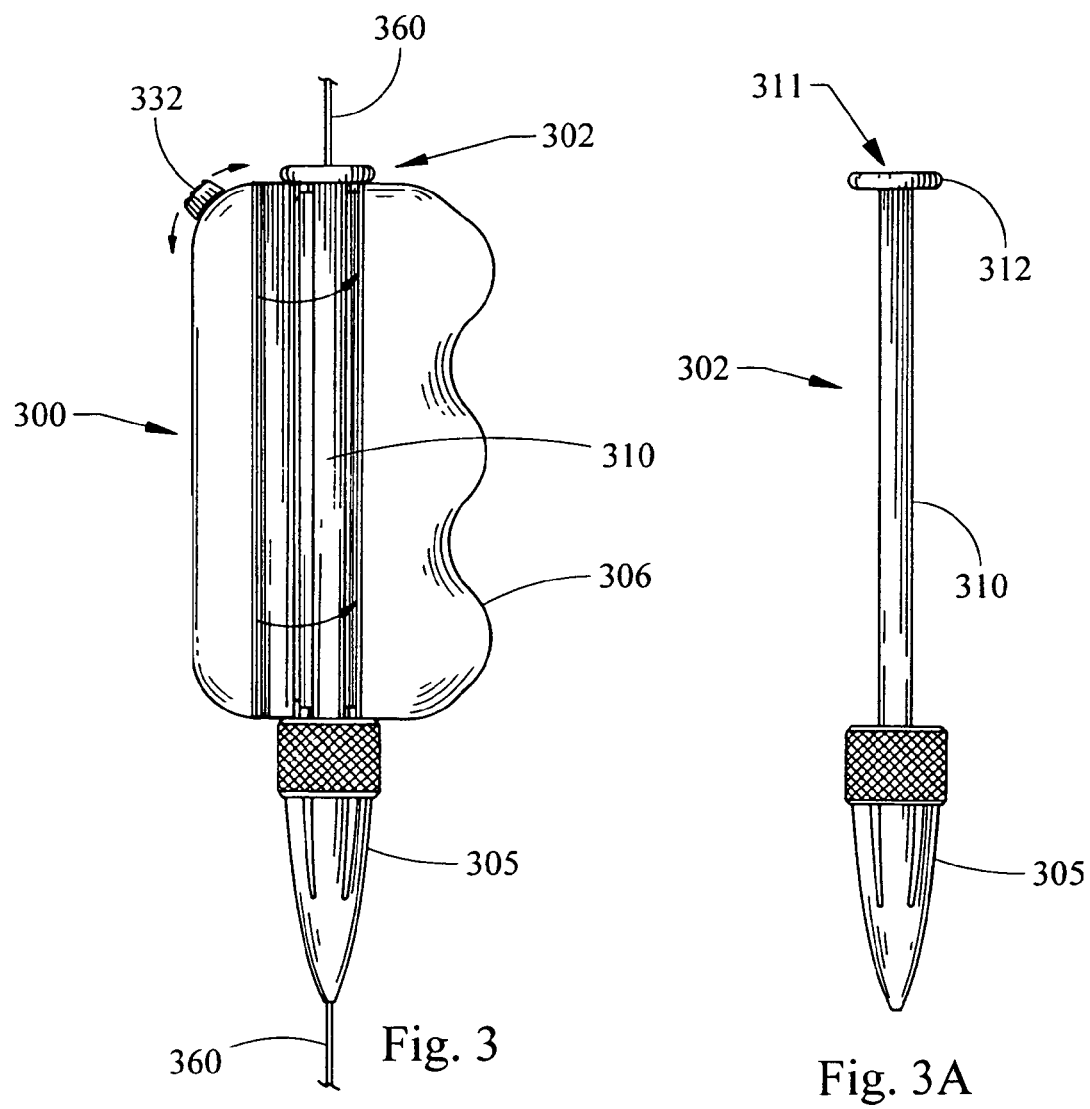
Fig. 3
Fig. 3A
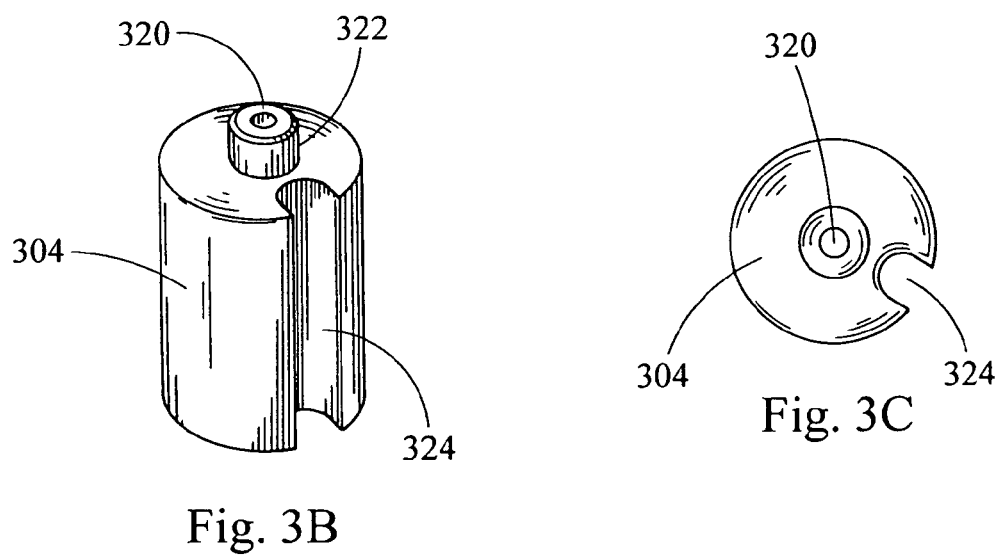
Fig. 3B
Fig. 3C

SPIRAL SHAFT CATHETER

CROSS-REFERENCE TO RELATED APPLICATIONS

This application claims priority to U.S. Provisional Application Ser. No. 60/737,181, filed Nov. 16, 2005, which is incorporated herein by reference in its entirety.

FIELD OF THE INVENTION

The present invention relates generally to medical devices and specifically to a catheter having a spiral shaft.

BACKGROUND

Medical delivery catheters are well-known in the art of minimally invasive surgery for the introduction of fluids and devices to sites inside a patient's body. A well-established technique, known as "long wire guide," is used for guiding a delivery catheter to a target site in a patient's body and it includes: (1) positioning a wire guide along a desired path to the target site; (2) retaining a proximal portion of the wire guide outside the body; (3) threading a delivery catheter, which has a wire guide lumen throughout its length, onto the proximal end of the wire guide; and (4) advancing the catheter along the wire guide to the treatment site.

One example of a desired path to a target site is the passage through a working lumen or channel of an endoscope to a biliary duct in a gastroenterological application. Another example of a desired path is through an endovascular lumen to an occluded coronary artery in a cardiology application. The delivery catheter may have a treatment device such as a stent or fluid-inflatable balloon disposed at its distal end for deployment at a target site (e.g., an occluded biliary duct or coronary artery). The catheter may also have a tool such as a cutting wire or cutting needle disposed at or near its distal end (e.g., a papillotome, sphincterotome, etc.), or the catheter may have an aperture for the delivery of a fluid through a second lumen (e.g., radio-opaque fluid for contrast fluoroscopy, adhesive or gelling agent for delivery to a target site, etc.).

Procedures that employ wire guides may require exchange of treatment appliances. For example, a balloon catheter may be replaced with a stent deployment catheter. In a typical application of such a procedure, a balloon catheter is directed to the site of a stenosis (e.g. in an artery, biliary duct, or other body lumen) as described above. Fluid is then used to inflate the balloon so as to dilate the stenosis. Some procedures are effectively concluded at this point. However, many procedures follow dilation of the stenotic stricture with the placement of a stent to maintain patency of the reopened lumen. This may require that the balloon catheter be withdrawn to allow for the introduction of a stent-deployment catheter (unless a stent placement catheter with an internal/placement balloon is used to accomplish both stenosis-dilation and stent-placement). It is preferable that the wire guide remain in place for guidance of the stent-deployment catheter without having to re-navigate the wire guide back into to the newly reopened lumen.

In order to prevent undesired displacement of the wire guide, any exchange of long wire guide catheters requires that the proximal portion of the wire guide extending out of the patient's body (or endoscope, depending on the entry point for the desired path to the target site) be longer than the catheter being "exchanged out," so that control of the wire guide may be maintained as the catheter is being removed. Likewise, the wire guide must be grasped while the entire catheter being "exchanged in" is threaded onto it and directed along the desired path to the target site. In other words, for the operating physician and assistant to be able to hold the wire guide in place while removing one catheter for replacement with another, each of the catheters must be shorter than the portion of the wire guide that is exposed outside the patient's body (and, if used, outside the endoscope). Put another way, the wire guide must be about twice as long as a catheter that is being used over that wire guide. Additionally, in the case of gastrointestinal endoscopy, even more wire guide length is necessary. This is because the shaft of the endoscope through which the wire guide and catheters are placed must have a length outside the body for manipulation and control, and the catheter itself must have some additional length outside of the endoscope for the same reason. As those skilled in the art will appreciate, wire guides having the necessary "exchange length" are cumbersome and difficult to prevent from becoming contaminated.

An alternative technique for guiding a delivery catheter to a target site in a patient body utilizes catheters having a relatively short wire guide lumen in catheter systems commonly referred to as "rapid exchange," "short wire guide," or "monorail" systems. In such systems, the wire guide lumen extends only from a first lumen opening spaced a short distance from the distal end of the catheter to a second lumen opening at or near the distal end of the catheter. As a result, the only lumenal contact between the catheter's wire guide lumen and the wire guide itself is the relatively short distance between the first and second lumen openings. Several known advantages are conferred by this configuration. For example, the portion of the wire guide outside the patient's body may be significantly shorter than that needed for the "long wire configuration." This is because only the wire guide lumen portion of the catheter is threaded onto the wire guide before directing the catheter through the desired path (e.g., a working lumen of an endoscope, an endoluminal passage, etc.) to the target site.

By way of illustration, the prior art catheters pictured in FIGS. 1A and 1B illustrate the distal ends of two different types of typical catheters. FIG. 1A shows the distal end of a prior art long-wire catheter shaft 100 with a wire guide 102 disposed in a lumen 104. The lumen 104 extends substantially to the proximal end (not shown) of the catheter shaft 100. In certain rapid exchange catheter configurations, the wire guide lumen is open to a side port aperture located on the side of the catheter between its proximal and distal ends. In one such configuration, the wire guide lumen only extends from the side port aperture to an opening at the distal end. An example of this type of rapid exchange catheter is illustrated in FIG. 1B.

FIG. 1B shows the distal end of a prior art short-wire catheter shaft 110 with a side port aperture 111 and a wire guide 112 disposed in a lumen 114. The length of the lumen 114, and consequently the exchange length of the catheter 110, is substantially shorter than that of the catheter 100 shown in FIG. 1A. In addition to a shorter exchange length, the catheter 110 (FIG. 1B) provides a reduced surface contact between the wire guide and catheter lumen that results in a reduced friction between the two. This can result in an eased threading and exchange process by reducing the time and space needed for catheter exchange. This economy of time and space is advantageous for minimally invasive surgeries since it reduces the likelihood of contamination and reduces the total time and stress of completing surgical procedures. On occasion, when advantageous, a catheter (such as, for example, the catheter 100 in FIG. 1A) may be left in place while the first wire guide is removed and replaced with a second wire guide; or, the wire guide lumen may be used for another purpose such as injecting a contrast media.

In another type of rapid exchange catheter configuration, the wire guide lumen extends through the length of the catheter from near its proximal end to its distal end. A side port aperture between the proximal and distal ends opens into the wire guide lumen. This side port aperture allows the catheter to be used in a short wire guide configuration, while the full-length wire guide lumen allows the catheter to be used in a long wire guide configuration. This wire guide lumen configuration is referred to as "convertible" or "dual use." An example of this type of catheter is illustrated in FIG. 1C, which shows the distal end of a prior art "dual use" catheter shaft 120 with a wire guide 122 disposed through a side port aperture 121 and into a wire guide lumen 124. Specifically, a wire guide may run through substantially the entire length of the wire guide lumen, or the wire guide may run only through the portion of the lumen between the distal end and the side port aperture. In each of the described prior art embodiments, the side port aperture is located in a single, predetermined position relative to the ends of the catheter.

It would be advantageous to provide a catheter, such as an inflation balloon catheter, with a structure allowing multiple locations for the entry or exit of a wire guide for use in a rapid exchange configuration or long wire configuration.

BRIEF SUMMARY

In one aspect, the present invention includes embodiments of catheters, including balloon catheters, with spirally/helically coiled body lengths. Portions of the catheter body length may be straight or may have a different helical pitch than other portions of the catheter body length. In a preferred aspect, a catheter device is provided and includes a proximal end and a distal end with a catheter shaft therebetween, with the catheter shaft including at least one helically coiled portion. In another aspect, the present invention includes embodiments of devices for directing a spiral body catheter along a wire guide.

BRIEF DESCRIPTION OF THE DRAWINGS

FIG. 3 is a first embodiment of a catheter advancement device;
FIG. 3A is a central shaft member of the catheter advancement device of FIG. 3;
FIG. 3B is a side view of a grooved cylinder of the catheter advancement device of FIG. 3;
FIG. 3C is an end view of a grooved cylinder of the catheter advancement device of FIG. 3;
FIG. 5A is a cross-sectional view along line 5A-5A of FIG. 5;
FIG. 5B is a wire guide clamp unit;
FIG. 5C is a detail view of FIG. 5, showing the placement of a wire guide and wire guide clamp.

DETAILED DESCRIPTION

Figure 1A:
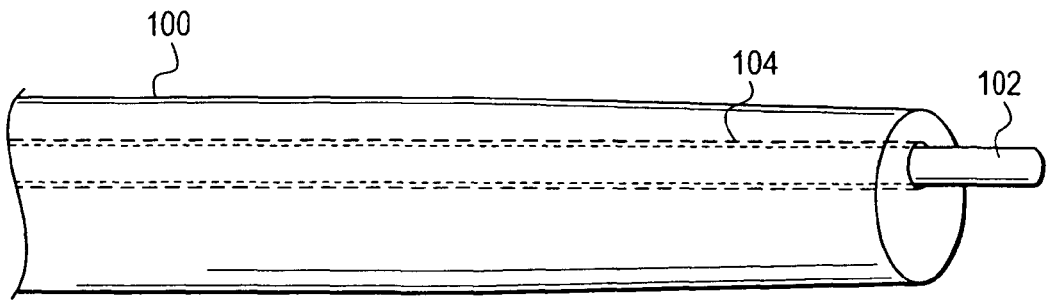
FIG. 1A is a prior art long-wire catheter.
Figure 1B:
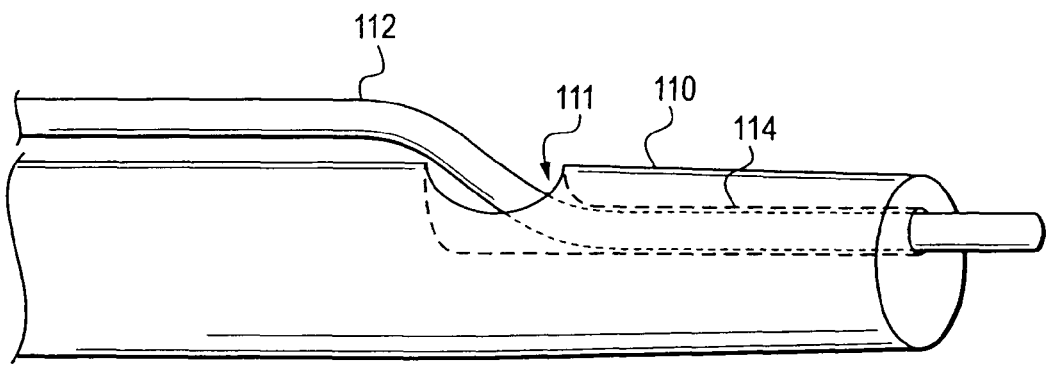
FIG. 1B is a prior art short-wire catheter.
Figure 1C:
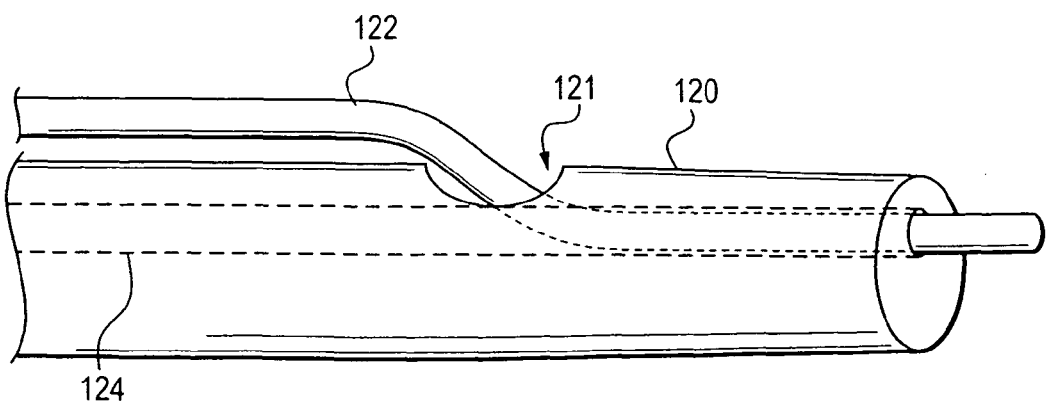
FIG. 1C is a prior art dual use catheter.
Figure 2:
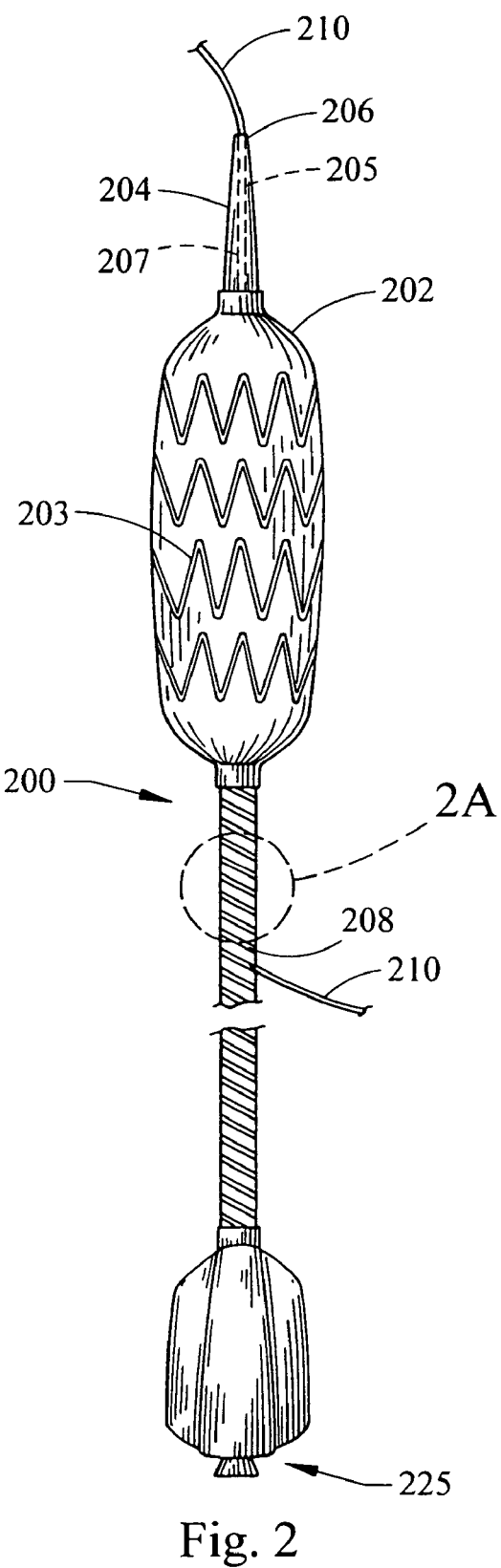
FIG. 2 is a first embodiment of a spiral shaft balloon catheter.
Figure 2A:
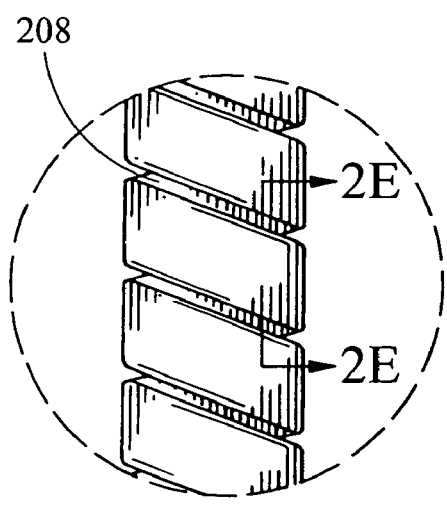
FIG. 2A is an enlarged view of a helical portion of the spiral shaft catheter of FIG. 2.

A first embodiment of a spiral shaft catheter device 200 is illustrated in FIGS. 2-2A. The catheter 200 includes an expandable member, specifically, a fluid-expandable member that is embodied as a balloon 202 that can be used, for example, for dilation of strictures, stent delivery, or stent extraction. As illustrated, the balloon 202 is surrounded by a stent 203, configured for placement in, for example, a vessel stenosis. The catheter 200 includes a two-part shaft. A distal catheter portion 204 is generally straight and extends from the distal catheter end 206 through and to about the proximal end of the balloon 202. The distal catheter portion 204 includes a first distal lumen 205 configured to allow passage of a wire guide 210 and a second distal lumen 207 open to the distal end to allow passage of, for example, radio-opaque contrast fluid. A tight-spiral catheter portion 208 extends proximally from about the proximal end of the balloon 202 and is generally helically shaped. A balloon or other expandable member for use with the present invention may include flexible/distensible material such as, for example, latex or silicone, and/or may include non-distensible material such as, for example, PET or nylon. The expandable member may be embodied as a balloon (as described above) or as another fluid-activated member.

In the illustrated embodiment, shown in enlarged detail in FIG. 2A, the spiral portion 208 includes a series of coils with a rounded rectangular profile configured like, for example, the cord commonly found between the handset and base of a telephone. The cross-sectional view of FIG. 2E (taken along line 2E-2E of FIG. 2A) shows that the spiral portion 208 includes a first lumen 220 configured to allow passage of, for example, inflation fluid through the catheter to the interior of the balloon 202, and a second lumen 221 that is in fluid communication through a first aperture 217 with the second distal lumen 207 of the distal catheter portion 204. FIG. 2D illustrates a partially cut away side view of the balloon 202 in one embodiment of the described dual lumen configuration. The first lumen 220 opens into the interior of the balloon 202 through a second aperture 219. Those of skill in the art will appreciate that the illustrated design may be adapted to include only a single lumen, or more than two lumens, and will also appreciate that, within the scope of the present invention, there are alternative configurations for the lumens of the spiral catheter portion 208 to connect in fluid communication with the lumens of the distal catheter portion 204. The proximal end portion of the catheter 200 includes a fluid-introduction hub 225 for allowing introduction of fluid through the catheter lumens 220, 221. The catheter preferably includes materials that provide desirable pushability and trackability (e.g., polyurethane, PTFE, silicone, nitinol, other alloys).

Figure 2B:
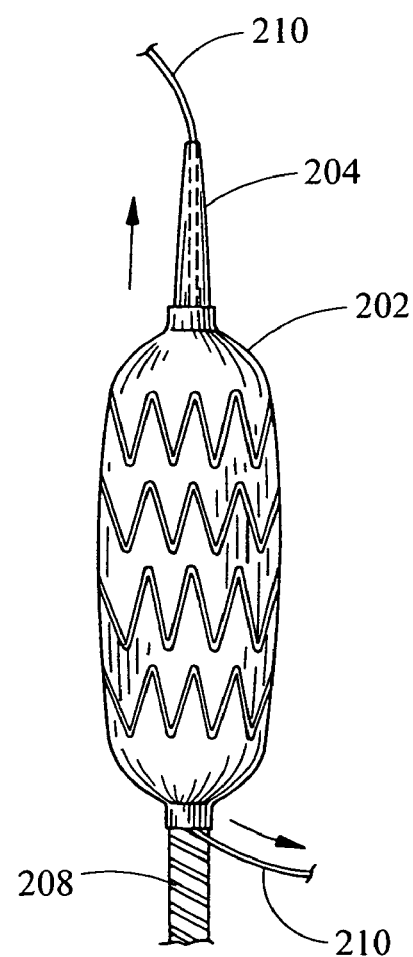
FIG. 2B is a detail view of the catheter of FIG. 2, showing passage of a wire guide therethrough.
Figure 2C:
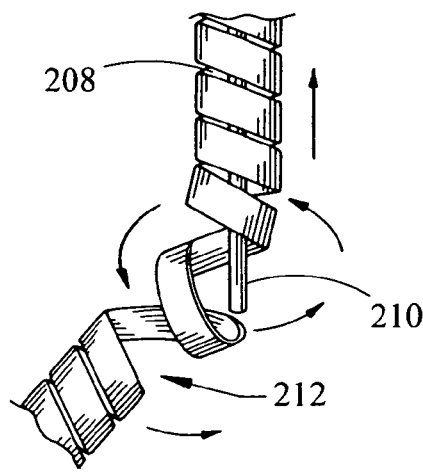
FIG. 2C is an enlarged detail view of the catheter of FIG. 2, showing winding advancement of the catheter along a wire guide.
Figure 2D:
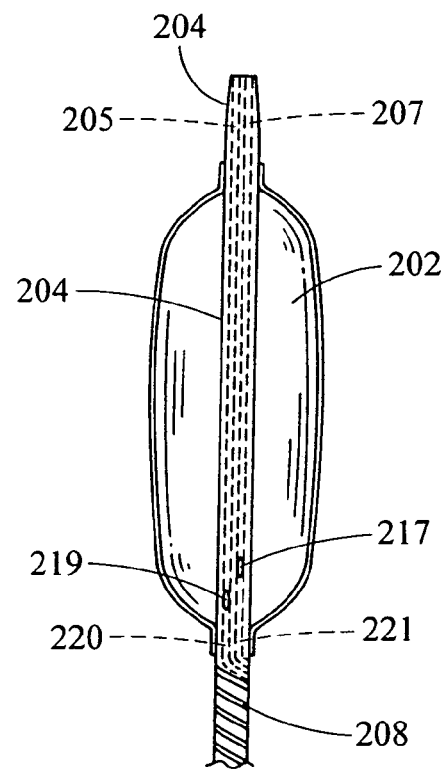
FIG. 2D is a longitudinal cross-sectional view of the balloon of the catheter of FIG. 2.
Figure 2E:
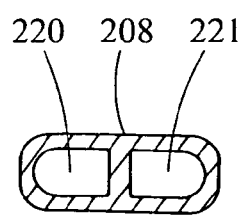
FIG. 2E is a cross-sectional view of the spiral catheter, taken along line 2E-2E of FIG. 2A.

As shown in FIGS. 2B-2C, the inner surface of the spiral portion 208 forms a wire guide tracking region 212 along the central longitudinal axis of the catheter 200 through which the wire guide 210 may be directed to or directed from the first distal lumen 205 of the distal catheter portion 204. In a relaxed default position, the coils of the spiral portion 208 are close together with little or no significant space therebetween. For example, the helical coils of the spiral portion 208 may have a pitch such that a gap between adjacent coils is less than or equal to the longitudinal width of the adjacent coils. However, the coils of the spiral portion 208 preferably are sufficiently flexible so that they may be opened to allow passage of the wire guide 210 from the tracking region 212 to the exterior of the spiral portion 208. When the wire guide 210 is passed between the coils, the catheter 200 may be advanced or retracted along the wire guide 210 by rotation. Specifically, and as shown in detail in FIG. 2C, orientation of the wire guide 210 between the coils of the spiral portion 208 allows a screw-like advancement or retraction of the catheter 200 along the wire guide.

In one application, illustrated with reference to FIGS. 2B-2C, the distal end 206 of the catheter 200 can be advanced over a wire guide 210 such that the wire guide 210 passes through the lumen 205 of the distal catheter portion 204 that transits the balloon 202. The catheter 200 is then advanced such that the wire guide 210 passes through the tracking region 212 and is allowed to exit between adjacent coils of the spiral catheter portion 208. A user can determine how far proximally (along the length of the spiral catheter portion 208) the wire guide 210 remains in the tracking region 212 such that the wire guide 210 may exit immediately proximal of the balloon 202 (as shown in FIG. 2B) or at a location spaced more proximally from the balloon 202 (as shown in FIG. 2).

After the wire guide 210 extends out from between the coils of the spiral catheter portion 208, the catheter 200 may be advanced in either or both of two ways: (a) the catheter 200 may be pushed distally along the wire guide 210 in the manner of catheters now in use (i.e., the gap between the coils functioning as a wire guide exit port); or (b) the catheter 200 may be rotated about its longitudinal axis such that the spiral catheter portion 208 is "screwed onto" or wound around the wire guide 210 in a manner that advances the catheter 200 distally along the wire guide 210. Preferably, the wire guide 210 is held in place during this operation so that it is not displaced from a selected location in a patient's body. The rotary advancement of the catheter 200 may be done by hand, or by use of a manual or powered mechanism that is configured to rotatingly advance the catheter 200 along the wire guide 210. FIGS. 3-5C show different embodiments of catheter advancement devices of the present invention.

Catheter embodiments may include visual indicia such as, for example, geometric shapes or colors and/or they may include radio-opaque indicia. These indicia may be used for classifying different catheter sizes, and they may be located at discrete pre-determined intervals along the distal and/or proximal portions of the catheter body so as to provide for visualization of metered advancement or retraction of the catheter when it is in use. For example, a series of markings may be used as described in U.S. Pat. No. 6,613,002, which is incorporated herein by reference.

The catheter structure provides for an ability to be rotatingly advanced using an appropriate catheter advancement means in a catheter advancement device, which may be manual or motorized. A first embodiment of a detachable catheter advancement device 300 is illustrated in FIGS. 3-3E. FIG. 3 depicts an exterior side view of the device 300. The catheter advancement device 300 includes a central shaft member 302, a motorized rotating member embodied as a cylinder 304 mounted longitudinally about the central shaft member 302, and an external body 306 that is mounted to a proximal portion of the central shaft member 302 and that houses a rotary motor (not shown).

As shown in FIG. 3, and in greater detail in FIG. 3A, the central shaft member 302 includes a proximal wire guide locking mechanism 305 disposed outside the proximal end of the external body 306, a hollow spindle 310 that passes longitudinally through a central portion of the external body 306, and a flanged distal end 312. The hollow portion of the spindle 310 forms a longitudinal wire guide lumen 311. The wire guide locking mechanism 305 may be, for example, a frictional twist-clamp or other type of locking mechanism.

Figure 3D:
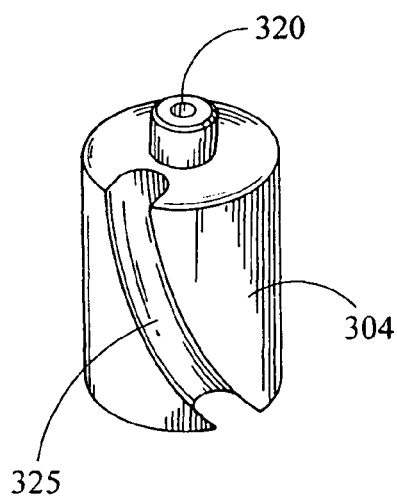
FIG. 3D is a side view of an alternative embodiment of a grooved cylinder of the catheter advancement device of FIG. 3.
Figure 3E:
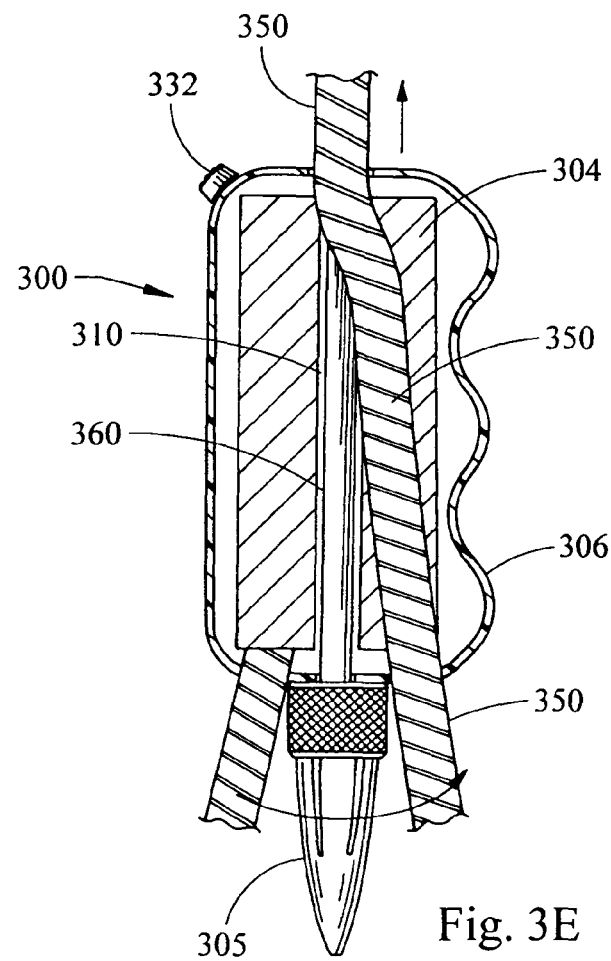
FIG. 3E is a longitudinal cross-sectional view of the catheter advancement device of FIG. 3.
Figure 3F:
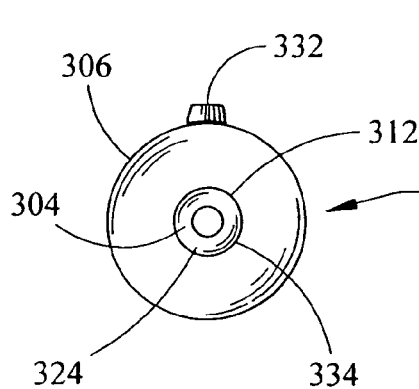
FIG. 3F is a distal end view of the catheter advancement device of FIG.3.

The rotating cylinder 304 is illustrated in greater detail in FIGS. 3B-3D. The cylinder 304 includes a central aperture 320 through which the shaft spindle 310 extends when the catheter advancement device 300 is assembled. As depicted in FIG. 3B, the cylinder 304 includes an optional threaded engagement structure 322 at its distal end to rotatingly engage the motor. In alternative embodiments, the engagement structure 322 may be toothed, or may be absent (e.g., if the motor for rotating the cylinder 304 is located inside of the cylinder). A groove 324 configured for feeding the catheter 300 along is located on a side of the cylinder 304. The groove 324 preferably is shallow at its proximal end and progressively deepens toward its distal end. FIG. 3C shows a distal end view of the cylinder 304 with the groove 324. Although, as shown in FIG. 3B, the groove 324 is generally straight and, although its depth increases proximally-to-distally, its length is generally parallel the longitudinal axis of the cylinder 304, FIG. 3D illustrates an alternative embodiment with a groove 325 that curves along the surface of the cylinder 304. Alternatively, the groove may have a consistent depth such that its longitudinal axis is substantially parallel to the central longitudinal axis of the cylinder 304. In an alternative embodiment, the motorized rotating member may be a shape other than cylindrical, provided that it includes a structure for rotating a helically coiled catheter in a manner that can advance/retract the catheter relative to a wire guide. Preferred embodiments will include a tracking structure that provides for smoothness of both the rotary and advancement/retraction motions relative to the rotating member.

As shown in FIG. 3, the external body includes a door 330, which may be sliding or hinged and is configured to allow placement of a catheter 350 into the groove 324 of the cylinder 304. A switch 332 is included for turning on/off the rotation motor and for changing the direction of rotation. The body 306 is generally cylindrical, and preferably includes an ergonomic grip shape configured such that a user may conveniently grasp the device 300 and operate the switch 332 with his thumb. FIG. 3F illustrates a distal end view of the catheter advancement device 300, showing a generally circular distal aperture 334 of the body 306. The flanged end 312 of the shaft member 302 and the distal end of the cylinder 304 with groove 324 are visible through the distal body aperture 334. FIG. 3G depicts a proximal end perspective view of the device 300, showing the wire guide locking mechanism 305.

Figure 3G:
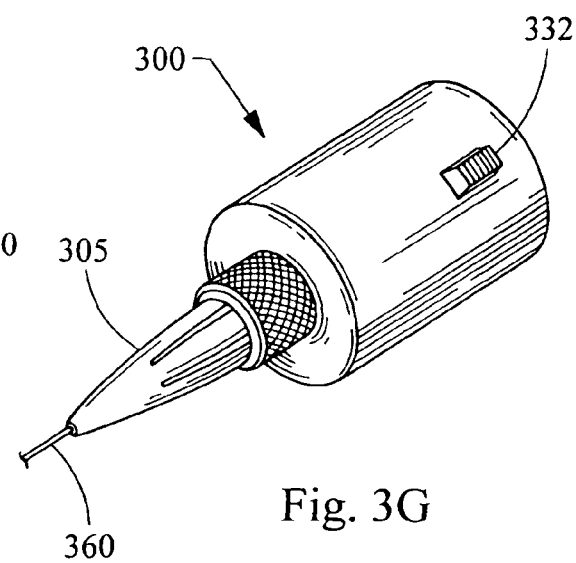
FIG. 3G is a perspective proximal end view of the catheter advancement device of FIG. 3.

Operation of the catheter advancement device 300 is explained here with reference to FIGS. 3-3G, especially FIG. 3E, which is a partial cross-sectional side view of the catheter advancement device 300. To operate the device, a user directs a wire guide 360 into a desired location in a patient and directs the catheter 350 (e.g., a non-balloon catheter or a balloon catheter similar or identical to the catheter 200 shown in FIG. 2) over the wire guide 360. Then the user mounts the catheter advancement device 300 onto the wire guide 360 such that the wire guide 360 is threaded through the central shaft member 302. The user then engages the wire guide locking mechanism 305 to hold the catheter advancement device 300 static relative to the wire guide 360. In one embodiment (not shown), the catheter advancement device 300 or a harness therefor may be configured to mount to a medical device that facilitates access into the patient (e.g., an endoscope, a minimally invasive surgical port), thereby enhancing the stability of the wire guide 360 and the catheter advancement device 300. The user opens the door 330, actuates the motor using the switch 332 so that the motor rotates the central cylinder 304 until the groove 324 of the central cylinder 304 is aligned with the door opening 330 and positions the catheter 350 along the groove 324. The spiral catheter 350 preferably has at least one or two of its coils engaged around the wire guide 360. The door 330 is closed and the motor may then be actuated to advance the catheter 350 distally along the wire guide 360 as the cylinder 324 is rotated to wind the spiral catheter 350 onto the wire guide 360. The motor may also be operated in reverse to unwind the spiral catheter 350 from the wire guide 360, thereby retracting the catheter 350. Once one or more of the coils of the spiral catheter 350 are engaged around the wire guide 360, the catheter 350 may be advanced distally or retracted proximally by respectively pushing or pulling the catheter 350 along the wire guide 360 in the same manner as traditional rapid exchange catheters. One advantage of using the winding advance/retract feature afforded by the spiral catheter design is that the catheter 350 may be advanced or retracted with one hand using the motor. This is possible because the wire guide 360 is held in place by the device 300 and the motor works to advance/retract the catheter 350 along the wire guide 360. Another advantage is that manual or motor-driven advancement/retraction of the catheter 350 may be accomplished very precisely in very small increments.

Figure 4A:
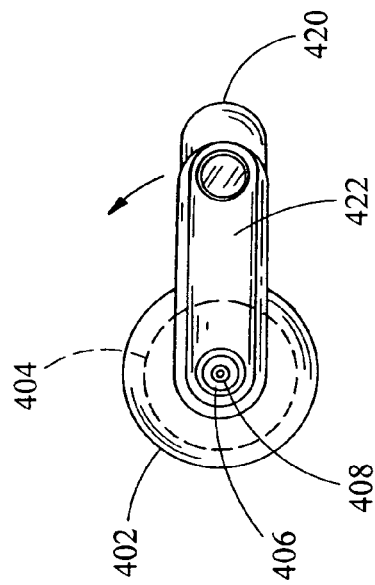
FIG. 4A is a distal end view of the catheter advancement device of FIG.4.
Figure 4:
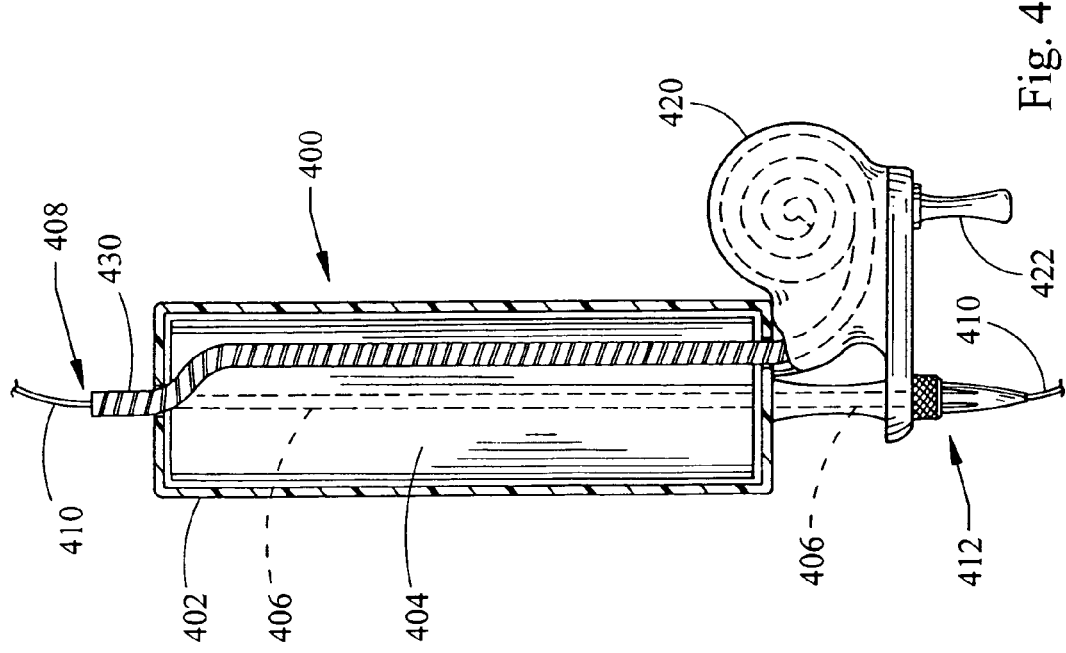
FIG. 4 is a partial longitudinal cross-sectional view of a second embodiment of a catheter advancement device.

FIGS. 4-4A depict a second embodiment of a detachable catheter advancement device 400. The catheter advancement device 400 includes a generally cylindrical grip/housing 402 that houses a grooved rotating cylinder 404, which is mounted rotatingly about a central shaft 406. The central shaft 406 includes a longitudinal wire guide lumen 408 to allow passage of a wire guide 410 and a wire guide locking mechanism 412 at its distal end. In an alternative embodiment, a wire guide locking mechanism may be provided separately from the catheter advancement device 400. A catheter holder/feeder 420 is mounted rotatably to the distal end of the central shaft 406. The holder/feeder 420 is configured to hold a rolled-up spiral catheter 430 such that, when the catheter advancement device 400 is actuated, the catheter 430 can be fed out through the grip/housing 402 and advanced distally along the wire guide 410.

As illustrated, the holder/feeder 420 includes a crank handle 422 for manual rotation thereof so as to facilitate deployment of the catheter 430. The holder/feeder 420 is also attached to the grooved cylinder 404 such that an opening from the holder/feeder 420 is aligned with the groove 405 [Note: 405 is not labeled in FIG. 4 or FIG. 4A] of the cylinder 404. This attachment and alignment is configured such that, when the holder/feeder 420 is rotated, the cylinder 404 also rotates in a manner that advances the catheter 430 distally along the wire guide 410. FIG. 4A shows a distal end view of the catheter advancement device 400. Actuation of the catheter advancement device 400 includes a user grasping the grip/housing 402 in one hand and rotating the crank handle 422 with the other hand such that the grip/housing 402 and the cylinder 404 cooperate to advance the catheter 430, uncoiling it from the holder/feeder 420. In an alternative embodiment, a motor may be mounted to rotate the holder/feeder 420 and cylinder 404, rather than the manual crank handle 422.

Figure 5:
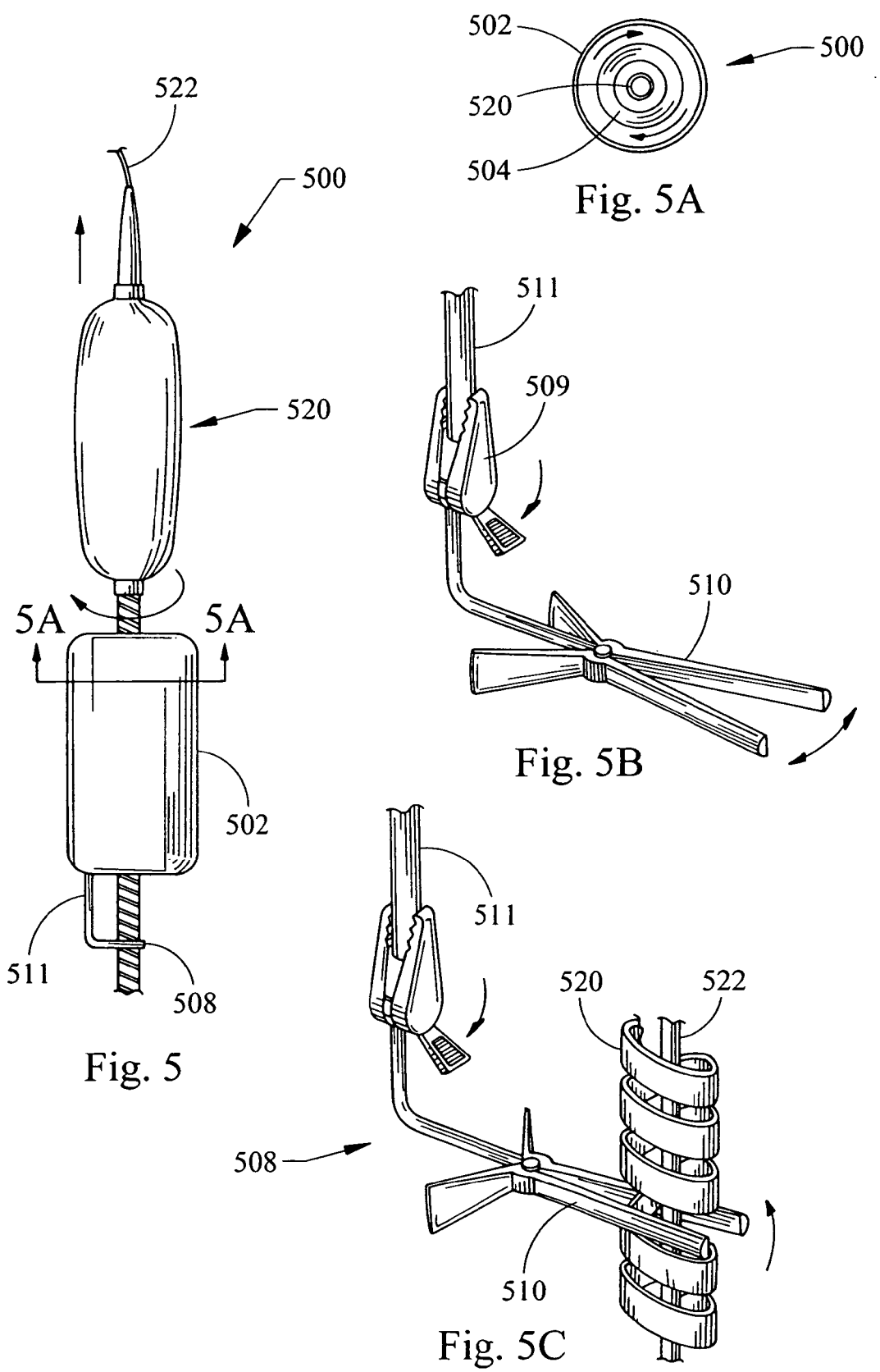
FIG. 5 is a third embodiment of a catheter advancement device.

FIGS. 5-5C show a third embodiment of a detachable catheter advancement device 500. The body 502 of the catheter advancement device 500 contains a motor that rotates a rotary grasping means 504 (e.g., a sleeve, a set of rollers, or some other appropriate structure with a surface frictionally sufficient to rotate a spiral catheter of the present invention). The structure of the catheter advancement device 500 is shown most clearly with reference to the side view of FIG. 5 and the transverse cross-sectional view in FIG. 5A (taken along line 5A-5A of FIG. 5). A balloon catheter 520 having a spiral proximal portion (for example, similar to the catheter device 200 described with reference to FIGS. 2-2C) may be fed longitudinally through the catheter advancement device 500 and then advanced over a wire guide 522. A wire guide clamp 510 of a clamp unit 508, shown in FIG. 5B, is mounted by a base clamp 509 to a proximal bracket 511 of the catheter advancement device 500. The base clamp 509 alternatively may be mounted to a different structure, such as an endoscope accessory. The wire guide clamp 510 is passed through the spiral portion and clamped to the wire guide 522, as shown in FIG. 5C. Although the position of the wire guide clamp 510 is shown proximally of the body 502 of the catheter advancement device 500, the wire guide clamp 510 from the spiral portion of the catheter 520 may be distal of the catheter advancement device body 502.

During operation of the catheter advancement device 500, the motor is actuated such that the rotary grasping means 504 turns to rotate the catheter 520. The wire guide clamp 510 holds the wire guide 522 in place during this operation such that the rotation of the spiral catheter 520 causes it to advance distally in an auger-like fashion as it is screwed past the static engagement position of the clamp 510 and wire guide 522.

Figures 6, 6A:
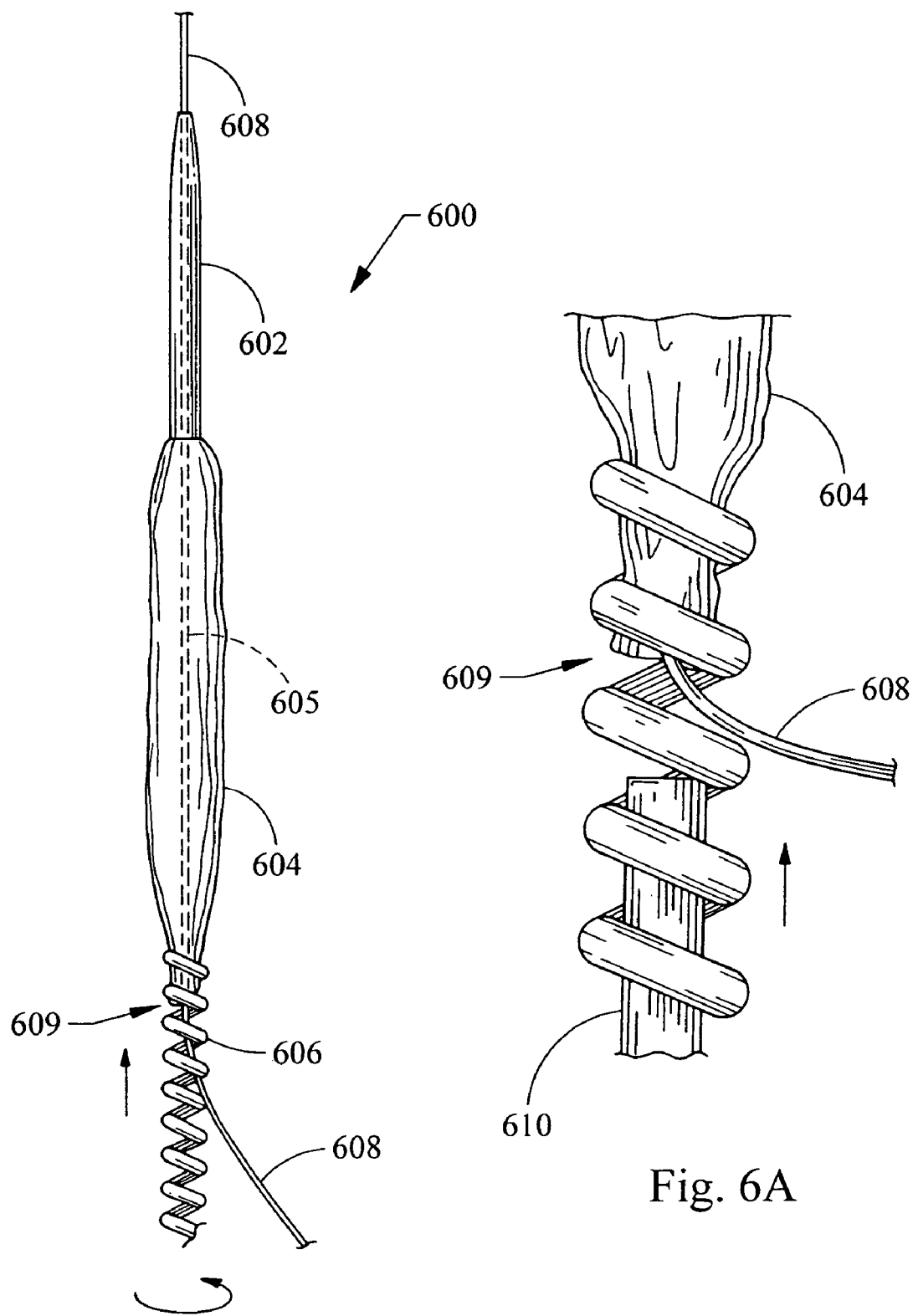
FIG. 6 is a second embodiment of a spiral balloon catheter.
FIG. 6A is a detail view of FIG. 6, showing an optional stiffener.

FIGS. 6-6A illustrate a second embodiment of a spiral balloon catheter 600. The catheter 600 includes a distal tip portion 602, a balloon 604 with a central wire guide lumen 605 therethrough, and a spiral body portion 606. The catheter 600 is shown with a wire guide 608 passed along the central tracking region 609 and exiting between adjacent coils of the spiral portion 606. In contrast with the tight-spiral catheter portion 208 of the catheter shown in FIG. 2, the spiral portion 606 has spaces between each of the adjacent coils along its length. Preferably, the pitch of the spiral portion 606 is such that the coils are sufficiently spaced to allow a wire guide passage therebetween. For example, the helical coils of the spiral portion 606 may have a pitch such that a gap between adjacent coils is greater than or equal to the longitudinal width of the adjacent coils.

FIG. 6A depicts an optional removable stiffener 610 (e.g., tubular catheter, nitinol rod), which may be placed through the central tracking region 609 of the spiral portion 606. Placement of such a stiffener 610 may be useful for enhancing the pushability and trackability of the spiral portion 606.

Figure 7:
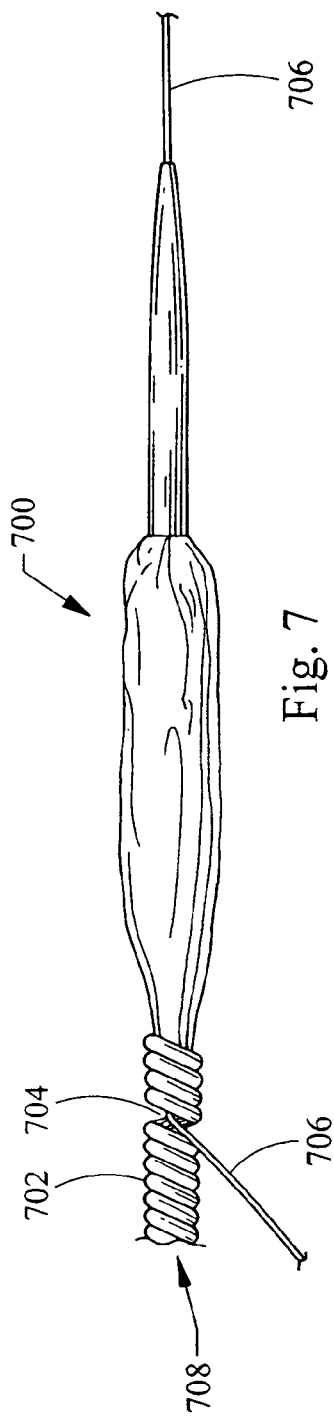
FIG. 7 is a third embodiment of a spiral balloon catheter.

FIG. 7 illustrates a third embodiment of a spiral balloon catheter 700. The spiral portion 702 is predominantly tightly spiraled, but includes one or more "looser" coils where the pitch of the spiral is steeper than that of the immediately adjacent coils, such that a gap 704 is provided between adjacent coils that allows for passage of a wire guide 706. This embodiment provides for use in a long-wire application, but is even more advantageous for use in short-wire applications, or anything in between, because the wire guide can be allowed to exit from the internal tracking region 708 of the spiral portion 702 anywhere along its length.

Figure 8A:
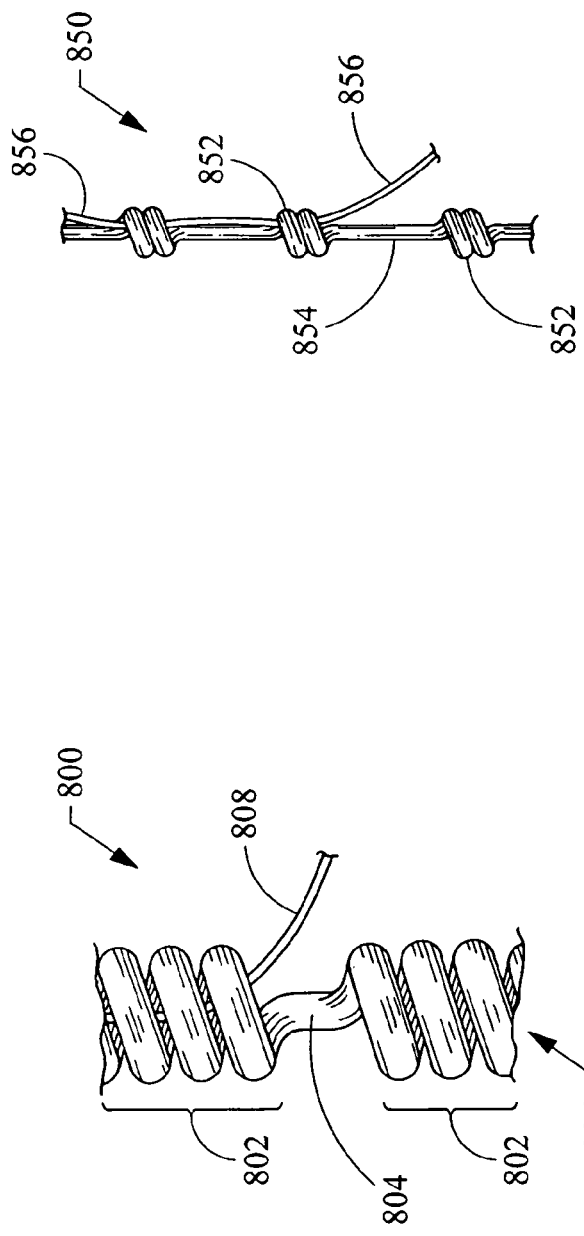
FIG. 8A is a second alternative embodiment of a catheter body.
Figure 8:
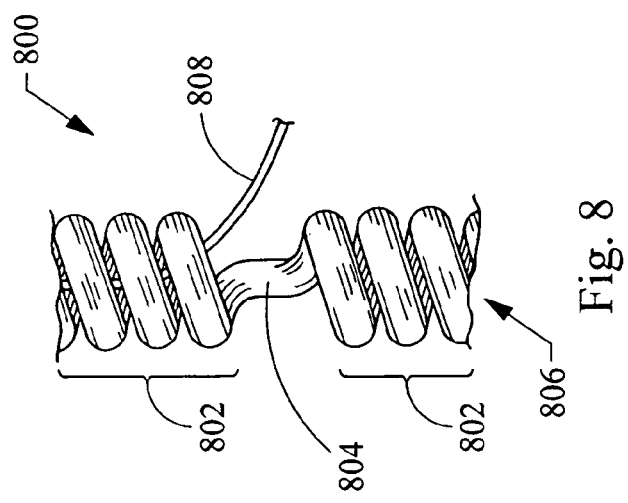
FIG. 8 is an alternative embodiment of a spiral catheter body.

FIGS. 8-8A depict alternative embodiments of a spiral catheter body 800 including predominantly spiraled portions 802. In the place of one or more coils, the catheter includes a short straight portion 804 that is open to the central tracking region 806 within the coils, allowing for passage of a wire guide 808. FIG. 8A shows a fifth embodiment of a catheter 850 wherein spiral coils 852 alternate along the catheter length with straight catheter portions 854. This structure allows a wire guide 856 to be run in close proximity to the catheter 850 for a user-determined length of the catheter 850. Thus, a user may use the catheter 850 in a short-wire or long-wire application, or somewhere in between.

Figure 9:
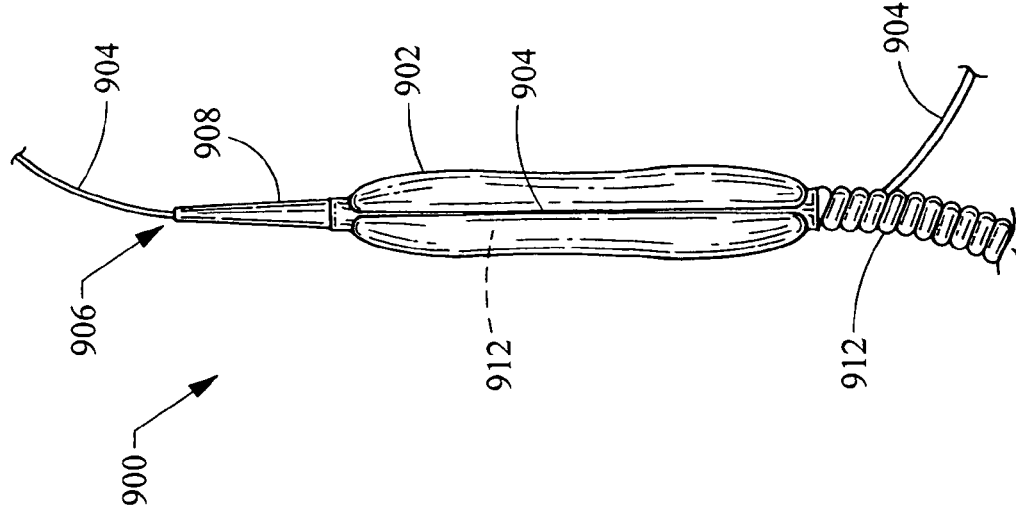
FIG. 9 is an alternative embodiment of a balloon.

FIG. 9 illustrates an alternative embodiment of a balloon 902 for use with a spiral body balloon catheter 900. Rather than having a wire guide lumen or cannula through the balloon 902 as described, for example, with reference to the balloon 202 illustrated in FIG. 2, the balloon 902 has an internal or external stiffener 912 (e.g., nitinol wire) that provides longitudinal rigidity to the balloon 902. The path of a wire guide 904 from a wire guide lumen 906 in the distal catheter tip portion 908 to the tracking region 910 of the spiral portion 912 is outside the balloon 902, which may include a fold, crease, or central passage.

Figure 10A:
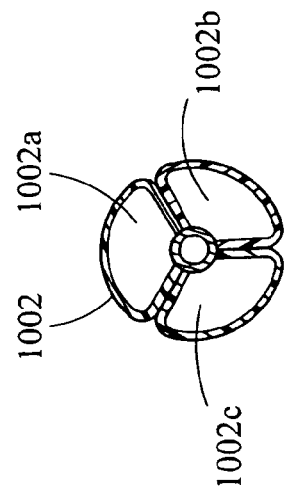
FIG. 10A is a transverse cross-sectional view along line 10A-10A of the balloon in FIG. 10.
Figure 10B:
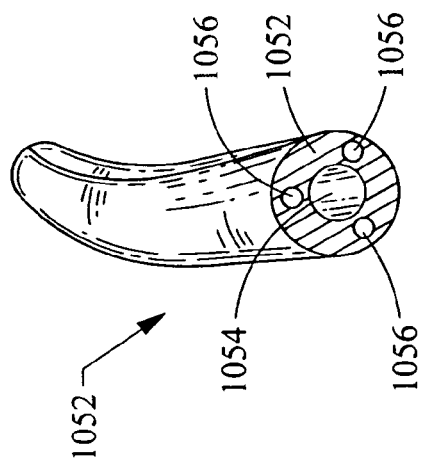
FIG. 10B is an alternative catheter body configured for use with the multi-chambered balloon of FIG. 10.
Figure 10:
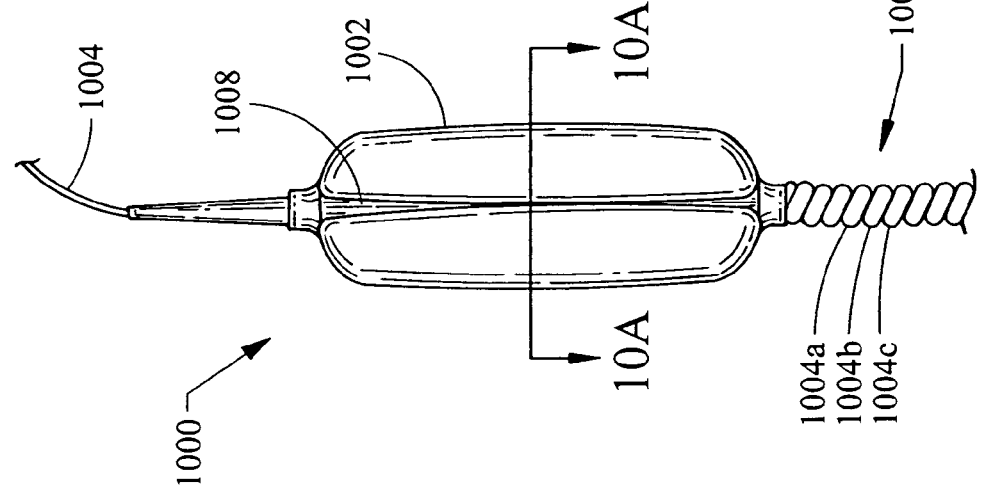
FIG. 10 is a fourth embodiment of a spiral balloon catheter, including a balloon with multiple independent chambers.

FIGS. 10-10A show another alternative embodiment of a balloon 1002 for use with a fourth embodiment of a spiral body balloon catheter 1000. As is more clearly shown in the transverse cross-sectional view of FIG. 10A (taken along line 10A-10A of FIG. 10), the balloon 1002 includes three independent chambers 1002a, 1002b, 1002c. The spiral portion 1004 of the catheter 1000 includes three separate catheter tubes 1004a, 1004b, 1004c spiraled together in parallel. The tubes 1004a, 1004b, 1004c of the spiral portion 1004 may be connected together to a single inflation fluid source, or may be connected independently to one or more sources of inflation fluid. This design provides a user with the ability to inflate the balloon 1002 in a nonsymmetrical manner by providing more fluid through one or two of the catheter tubes 1004a, 1004b, 1004c than through the other(s). More or fewer balloon chambers and catheter tubes could be provided as well, including one or more catheter tubes in the spiral section and passing through the balloon to provide for introduction of, for example, radio-opaque contrast fluid. This embodiment may be provided with a central cannula 1008 or other lumenal passage for passage of a wire guide 1006, or a wire guide may be passed between the balloon chambers; likewise, a stiffener (like that described with reference to FIG. 8) may be provided. Optional alternative embodiments of the catheter 1000 may include loose spirals (e.g., as in FIG. 6) or spaced coils (e.g., as in FIGS. 7, 8, and 8A).

As indicated in the partial cross-sectional view of FIG. 10B, the multi-chambered balloon design can also be used with a traditionally-shaped tubular catheter body 1050. The embodiment shown includes a thick catheter wall 1052 surrounding a central wire guide lumen 1054. The catheter wall 1052 includes three lumens 1056 configured to provide a path of fluid communication from a fluid source to, for example, the balloon.

The cross-sections of spiral catheter portions of the present invention may be rectilinear or rounded. Appropriate materials preferably are selected from materials that will provide desirable pushability and trackability. Extruded polytetrafluoroethylene, nitinol, stainless steel hypotube, multifilar cable, braided tubing, and combinations thereof are examples of materials that may be used.

It is therefore intended that the foregoing detailed description be regarded as illustrative rather than limiting, and that it be understood that the following claims, including all equivalents, are intended to define the spirit and scope of this invention.

I claim:

1. A catheter device, comprising:
a proximal end and a distal end with an elongate catheter shaft body disposed therebetween, the catheter shaft body formed as at least one set of a plurality of adjacent helical coils, where said set of coils defines both a central longitudinal region along an inward-facing surface of the at least one set of coils that is external to the catheter shaft body, an outward-facing surface of the at least one set of coils that is external to the catheter shaft body, and where said at least one set of coils includes at least one lumen internal to the catheter shaft body extending from the proximal end to the distal end.

2. The catheter device of claim 1, where the at least one set of coils comprises a plurality of sets of helical coils.

3. The catheter device of claim 2, wherein the sets of helical coils are separated by generally linear non-helical portions of the catheter shaft body.

4. The catheter device of claim 1, wherein the central longitudinal region provides a path for passage of a wire guide along a length of the catheter shaft body.

5. The catheter device of claim 1, wherein a proximal surface of each of the adjacent coils substantially contacts a distal surface of an immediately adjacent coil.

6. The catheter device of claim 1, wherein a proximal surface of each of the adjacent coils is spaced apart from a distal surface of an immediately adjacent coil, forming a gap therebetween that is a selected one of less than, greater than, or equal to a longitudinal width of each of the adjacent coils.

7. The balloon catheter device of claim 6, wherein the adjacent coils have a predetermined pitch such that a gap exists between the adjacent coils and the gap is sized to allow passage of a wire guide.

8. The catheter device of claim 1, further comprising an expandable member disposed adjacent the distal end, and wherein the at least one lumen internal to the catheter shaft body is in patent fluid communication with the expandable member.

9. The catheter device of claim 8, wherein the expandable member is a fluid-expandable member.

10. The catheter device of claim 9, further comprising a wire guide cannula disposed adjacent a length of the fluid-expandable member.

11. The catheter device of claim 9, wherein a wire guide cannula is disposed through a central portion of the fluid-expandable member.

12. The catheter device of claim 9, wherein the fluid-expandable member is a balloon that comprises at least two separate balloon chambers.

13. The catheter device of claim 12, wherein the catheter shaft body comprises parallel catheters substantially equal in number to the number of balloon chambers, and wherein each parallel catheter is in fluid communication with one of the balloon chambers.

14. The catheter device of claim 9, further comprising at least one of a wire guide cannula disposed through an interior portion of the fluid-expandable member, a stiffening member disposed adjacent a lengthwise portion of the fluid-expandable member, and a stent device.

15. The catheter device of claim 1, further comprising a removable stiffening member disposed through the central longitudinal region.

16. The catheter device of claim 1, further comprising a detachable catheter advancement device, the catheter advancement device comprising:
a central shaft member, a catheter-guiding member rotatably disposed around the central shaft member, and a means for rotating the catheter-guiding member, said means selected from a motor means and a manual turning/crank means.

17. The catheter advancement device of claim 16, wherein the catheter-guiding member comprises a grooved cylinder.

18. The catheter advancement device of claim 17, wherein a groove of the grooved cylinder is substantially parallel to the longitudinal axis of the cylinder.

19. The catheter advancement device of claim 17, wherein a groove of the grooved cylinder is deeper near the distal end of the longitudinal axis of the cylinder than near the proximal end of the longitudinal axis of the cylinder.

20. The catheter advancement device of claim 16, further comprising a wire guide locking mechanism.

21. The catheter advancement device of claim 16, wherein the central shaft member includes a wire guide lumen disposed centrally therethrough.

22. The catheter advancement device of claim 21, further comprising a catheter storage unit attached to the rotating means and configured to allow a catheter stored in the catheter storage unit to be fed through a groove of the grooved cylinder such that the plurality of helical coils defining the central longitudinal region are coiled around a wire guide disposed through the wire guide lumen.

23. The catheter device of claim 1, further comprising:
a balloon with at least first and second independent balloon chambers; and
the at least one lumen internal to the catheter shaft body extending proximally from the balloon, the at least one lumen being defined by a wall with a predetermined thickness;
the at least one lumen internal to the catheter shaft body comprising at least a first lumen and a second lumen extending from the proximal end to the distal end, the first lumen in fluid communication with the first independent chamber and the second lumen in fluid communication with the second independent chamber.

24. The catheter device of claim 23, further comprising a third independent balloon chamber and wherein the at least one lumen internal to the catheter shaft body includes a third lumen in the wall, said third lumen in fluid communication with the third independent balloon chamber.

* * * * *